(12) United States Patent
Zimmerman

(10) Patent No.: US 7,794,417 B1
(45) Date of Patent: Sep. 14, 2010

(54) FOOTWEAR FOR MEDIALLY DIRECTING BIG TOE

(76) Inventor: Erik O. Zimmerman, 31925 Tracy Ln., Tavares, FL (US) 32778

( * ) Notice: Subject to any disclaimer, the term of this patent is extended or adjusted under 35 U.S.C. 154(b) by 0 days.

(21) Appl. No.: 12/215,195

(22) Filed: Jun. 24, 2008

Related U.S. Application Data

(60) Provisional application No. 60/958,018, filed on Jul. 2, 2007.

(51) Int. Cl.
*A61F 5/00* (2006.01)
(52) U.S. Cl. .......................... 602/23; 602/30
(58) Field of Classification Search ............ 602/23, 602/27, 28–30; 128/882; 36/101
See application file for complete search history.

(56) References Cited

U.S. PATENT DOCUMENTS

| 1,055,810 | A | * | 3/1913 | Scholl | 602/30 |
| 3,308,829 | A | * | 3/1967 | Edwards | 36/142 |
| 4,263,902 | A | * | 4/1981 | Dieterich | 602/30 |
| 4,300,294 | A | * | 11/1981 | Riecken | 36/97 |

OTHER PUBLICATIONS

Feet Relief, Bunion Night Splint From Apex, pp. 1 & 2 (www.feetrelief.com), downloaded Jul. 2, 2007.
Northwest Airlines, *Sky Mall*, p. 21, Autumn 2007.
Zimmerman, U.S. Appl. No. 60/958,018, filed Jul. 2, 2007 A.D.

* cited by examiner

*Primary Examiner*—Michael A. Brown
(74) *Attorney, Agent, or Firm*—Christopher John Rudy

(57) ABSTRACT

Footwear has strap for medially directing the big toe. The footwear may be in a form of a sandal; the strap may be adjustable; and a bunion deformity may be addressed.

4 Claims, 2 Drawing Sheets

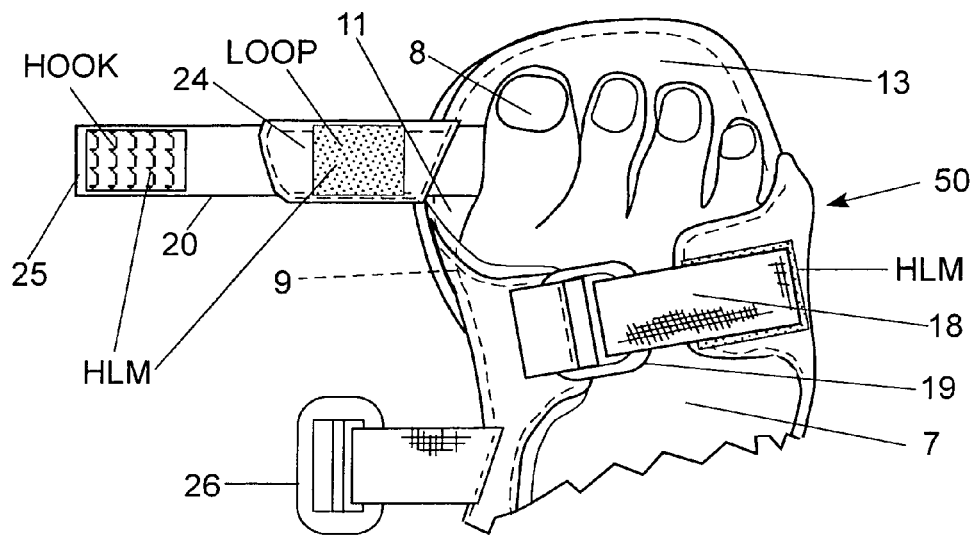
Fig. 3
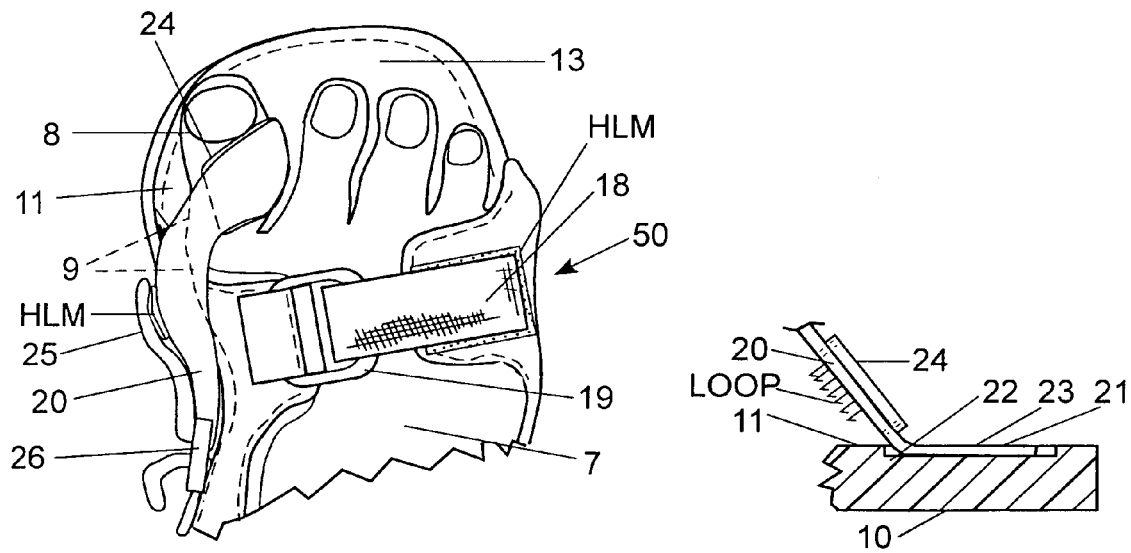
Fig. 4
Fig. 5

US 7,794,417 B1

FOOTWEAR FOR MEDIALLY DIRECTING BIG TOE

This claims the benefits under 35 USC 119(e) of U.S. provisional patent application No. 60/958,018 filed on Jul. 2, 2007 A.D. The complete specification of that application, including of course its drawings, is incorporated herein by reference.

FIELD AND PURVIEW OF THE INVENTION

The invention concerns footwear that has a strap to direct the first (big) toe medially. In one embodiment, the footwear is in the form of a sandal, and the strap is adjustable to go under and around the lateral side of the big toe and pull it medially, for example, to address a bunion deformity. The invention also concerns use of the same.

BACKGROUND TO THE INVENTION

A bunion (hallux abducto valgus) is a fairly common and frequently painful foot problem. Typically in such cases, the big toe (hallux) is presented at a "valgus" angle, i.e., pointed "outwardly," or laterally from the midline of the body. At the same time, the big toe joint of the first metatarsal and hallux points inwardly (medially). Various art is known to address bunions, and bring the deformed big toe into a more correct "varus" alignment or position, prominent among which is the art of bunion splints. See, e.g., Apex Bunion Night Splint (www.feetrelief.com).

Other art is known. Some art attempts to address bunions, other art does not.

Surgery is a common option. However, it can be painful and expensive.

In the field of footwear per se can be found the art of common sandals, which a bunion sufferer may opt to wear owing to a lack of pressure on the affected joint in relation to that pressure otherwise encountered from wearing closed footwear such as that of common boots and shoes. One form of a common sandal has a permanent, upstanding loop of material, for example, leather or plastic, affixed to the sole, through which the big toe is run. When such a sandal is worn, its loop can be found by the web of the foot by the large knuckle of the big toe. If a bunion sufferer were to wear a common sandal, even the loop-containing one, little if any help is provided to help orient the toe properly.

It would be desirable to improve upon or supply an alternative to the art.

A FULL DISCLOSURE OF THE INVENTION

In general, the present invention provides footwear that has a strap to medially direct the big toe. Provided also is use of the same.

The invention is a useful podiatric device.

Significantly, by the invention, the art is improved in kind. More particularly, the invention provides a simple, relatively safe device, which can address a bunion deformity. The footwear is inexpensive to make, and simple and pleasing in use.

Numerous further advantages attend the invention.

The drawings form part of the specification hereof. With respect to the drawings, which are not necessarily drawn to scale, the following is briefly noted:

FIG. 3 is a top view of the footwear of FIG. 1, with the strap lying medially under the valgus big toe of a bunion sufferer.

FIG. 4 is a top view of the footwear of FIG. 1, with the strap going under the big toe and around its lateral side, pulling it medially, with the free end of the strap affixed.

FIG. 5 is a cross-sectional view of the footwear of FIG. 1, taken along 5-5.

Figures 1, 2:
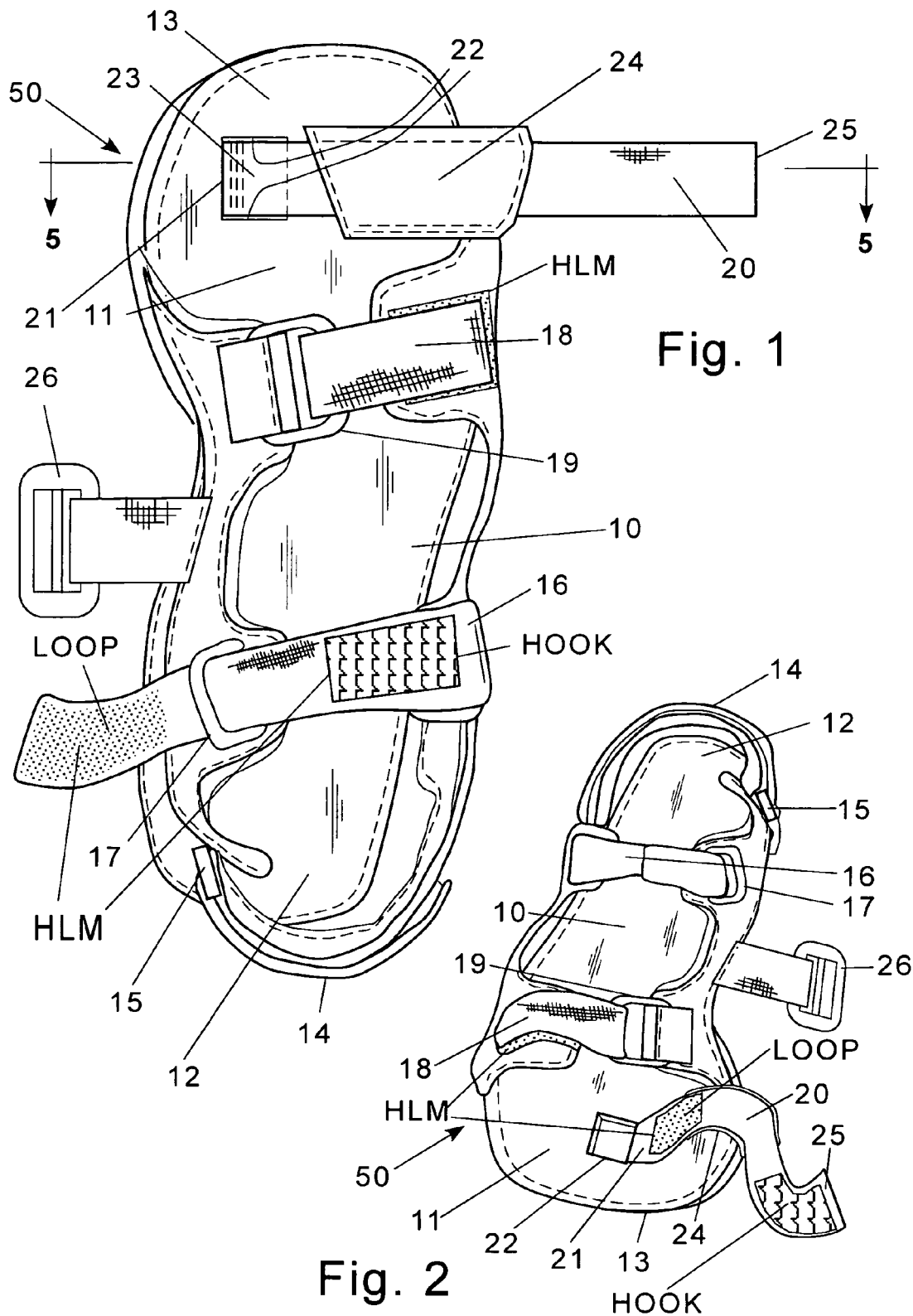
FIG. 1 is a top view of footwear for medially directing a big toe, which is embodied as a sandal, with a strap having a free end displayed as lying laterally.
FIG. 2 is a top view of the footwear of FIG. 1, with the strap lying medially.

The invention can be further understood by the detail set forth below, which may be read in view of the drawings. This, as with the foregoing, is to be read in an illustrative and not necessarily limiting sense.

The present footwear includes a strap to medially direct the big toe. The footwear may include closed toe styles such as boots and shoes, or open toe styles such as sandals. The strap may be non-adjustable or adjustable. The footwear may address a deformity such as a bunion or other condition that presents a varus big toe. The footwear can be in the form of a sandal, with the strap being adjustable to go under and around the lateral side of the big toe and pull it medially, for example, to address a bunion deformity.

Any suitable material(s) may be used, such as plastic, leather and/or cloth.

With respect to the drawings, footwear 50 can be embodied as one or both of a pair of sandals, for example, depicted for the right foot. Of course, the left would be a mirror image of the right. The footwear 50 can be worn on foot 7 to medially direct big toe 8, which may present bunion 9.

As a sandal, the footwear 50 can include sole 10 with upper surface 11. Rear end 12 and front end 13 are present. Depending on the style, there may be rear, heel strap 14, with heel strap fastener 15; full, middle strap 16, which would be close to the front of the ankle, with middle strap fastener 17; and full, front strap 18, which would generally cover all the larger knuckles close to the web of the foot, with front strap fastener 19.

The footwear 50 has big toe strap 20, which can be adjusted. The strap 20 has first end 21, which is affixed to the sole 10, say, about its upper surface 11, for example, by sewing. Other means to affix the first end 21 to the sole 10 may be employed in addition to or in lieu of sewing, for instance, clipping, pinning, stapling, riveting, gluing, melting or molding integrally with the sole 10 should it be made, say, of a plastic material. Big toe strap receiving notch 22 can be provided in the sole 10, for instance, to a depth about the thickness of the big toe strap 20 and for a suitable length such as that of about the width of half or more if not all or even more of the big toe 8, so that the big toe 8 is not discomfited by material of the big toe strap 20 that would lie directly upon the upper surface 11 of the sole 10 but rather rests more comfortably on inner surface 23 of the big toe strap 20 that is substantially coplanar with the upper surface 11 of the sole 10. Pad 24 may be provided to cushion the lateral side of the big toe 8 when the big toe strap 20 is fastened to pull the big toe 8 medially. The big toe strap 20 has second end 25, which can be initially free and then attached to instep fastener 26.

The fastener(s) 15, 17, 19, 26 may be in a form of a looping or other buckle. Hook and loop material (HLM) may assist in securing a looped fastener 15, 17, 19, 26.

Thus, the adjustable strap 20 with the sandal footwear 50 may aid a human being in the appearance, reduction or progression of a bunion deformity 9 of the big toe 8 of the foot 7. The strap 20 can go up the lateral side of the big toe 8 and progress over it to the fastener 26 on the instep of the sandal 50 for the medial side of the foot 7. The tension of the strap 20 shifts the big toe 8 medially, in the horizontal plane, which would encourage the medial soft tissue structures of the first metatarsophalangeal joint to shorten and align the big toe 8 in a more anatomically correct position.

The present invention is thus provided. Various feature(s), part(s), step(s), subcombination(s) and/or combination(s) may be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

What is claimed is:

1. A sandal for medially directing a big toe of a wearer of the sandal, which wearer has a foot with a heel, an ankle, knuckles close to a web of the foot, and the big toe, which toe has lateral and medial sides, which sandal comprises a sole having an upper surface, and front and rear ends; a rear, heel strap, with a heel strap fastener, a full, middle strap, close to a position of the sandal so as to be in front of the ankle of the wearer, with a middle strap fastener; a full, front strap, in a position of the sandal so as to generally cover all larger knuckles close to the web of the foot of the wearer, with front strap fastener; and a flexible strap to medially direct the big toe—wherein the strap has first and second ends, the first end of which strap is affixed to the front end of the sole and projects directly from the upper surface and front end of the sole to go around the lateral side of the big toe and pull it medially; and the second end of which strap can be attached to secure the big toe in a medially pulled position.

2. The sandal of claim 1, wherein the sandal has an instep and an instep fastener affixed about the instep; and the strap is adjustable, with the first end of which strap affixed to the sole about the upper surface of the sole and the second end of which strap capable of being initially free and then attached to the instep fastener, and the strap can go up the lateral side of the big toe and progress thereover to the instep fastener such that tension of the strap can shift the big toe medially, in a horizontal plane, so as to encourage medial soft tissue structures of a first metatarsophalangeal joint of the big toe to shorten and align the big toe in a more anatomically correct position.

3. The sandal of claim 2, wherein a strap receiving notch is provided in the upper surface of the sole in which the first end of the strap is fastened such that the big toe is not discomfited by material of the big toe strap that would otherwise lie directly upon the upper surface of the sole but rather rests more comfortably on an inner surface of the big toe strap that is substantially coplanar with the upper surface of the sole.

4. The sandal of claim 3, wherein a pad is provided the strap to cushion the lateral side of the big toe when the strap is fastened to pull the big toe medially.

\* \* \* \* \*